(12) United States Patent
Gold et al.

(10) Patent No.: US 8,858,993 B2
(45) Date of Patent: Oct. 14, 2014

(54) COATED TABLET WITH ZERO-ORDER OR NEAR ZERO-ORDER RELEASE KINETICS

(75) Inventors: Thomas B. Gold, Greenville, NC (US); Patrick Brian Woodall, Greenville, NC (US)

(73) Assignee: Metrics, Inc., Greenville, NC (US)

( * ) Notice: Subject to any disclaimer, the term of this patent is extended or adjusted under 35 U.S.C. 154(b) by 1188 days.

(21) Appl. No.: 11/488,547

(22) Filed: Jul. 18, 2006

(65) Prior Publication Data

US 2007/0020331 A1    Jan. 25, 2007

Related U.S. Application Data

(60) Provisional application No. 60/702,161, filed on Jul. 25, 2005.

(51) Int. Cl.
*A61K 9/20* (2006.01)
*A61K 9/22* (2006.01)
*A61K 9/28* (2006.01)

(52) U.S. Cl.
CPC ............. *A61K 9/2031* (2013.01); *A61K 9/2866* (2013.01)
USPC .......................................... 424/464; 424/468

(58) Field of Classification Search
CPC . A61K 9/2054; A61K 9/2866; A61K 9/2031; A01B 12/006
USPC .................................................. 424/464, 468
See application file for complete search history.

(56) References Cited

U.S. PATENT DOCUMENTS 4,505,890 A * 3/1985 Jain et al. ...................... 424/480
5,948,787 A 9/1999 Merrill et al.

(Continued)

FOREIGN PATENT DOCUMENTS

EP       0 277 092 B1    1/1992
WO    WO-2005/094794    10/2005

(Continued)

OTHER PUBLICATIONS

"POLYOX Water-Soluble Resins Dissolving Techniques" Dow Chemical Company, Published Mar. 2003, pp. 1-14.*

(Continued)

*Primary Examiner* — Aradhana Sasan
(74) *Attorney, Agent, or Firm* — Womble Carlyle Sandirdge & Rice; Mark D. Jenkins

(57) ABSTRACT

Tablets for the controlled release of an active ingredient in a zero-order or near zero-order fashion are provided. The tablet includes a core and a coating. The core includes at least one active pharmaceutical agent and a polyethylene oxide with a molecular weight of between about 1,000,000 and 10,000,000, preferably between about 4,000,000 and 8,000,000. The core material is optionally, but preferably, coated with a cellulosic material. The active pharmaceutical agent can be hydrophilic, hydrophobic, or amphiphilic. When the active pharmaceutical agent is a hydrophilic agent, it is preferred that the coating is a relatively hydrophobic cellulose, such as ethylcellulose or propylcellulose. However, if the tablet is uncoated, it can provide a near-zero-order release rate rather than a zero-order release rate. When the active pharmaceutical agent is a hydrophobic or amphiphilic agent, the hydrophilic polymeric carrier is the same as in the first embodiment, the coating is a relatively more hydrophilic cellulose. The release rate for the active pharmaceutical agent can be controlled by adjusting the thickness of the coating, and, optionally, by adjusting the concentration of the polymeric excipients, as well as certain non-polymeric excipients which may optionally be present. An advantage of using relatively high molecular weight polyethylene oxide is that the release is pH independent, unlike where ionic polymers such as polyacrylic acids are used. Further, active pharmaceutical agents including functional groups that might react with such polymers can be used without an adverse reaction between the active agent and the polymer.

9 Claims, 2 Drawing Sheets

Formulation A

(56) References Cited

U.S. PATENT DOCUMENTS

| | | | |
|---|---|---|---|
| 6,048,547 A * | 4/2000 | Seth et al. | 424/464 |
| 6,068,859 A * | 5/2000 | Curatolo et al. | 424/490 |
| 6,500,459 B1 * | 12/2002 | Chhabra et al. | 424/474 |
| 2003/0175353 A1 | 9/2003 | Dudhara et al. | |
| 2005/0074487 A1 | 4/2005 | Hsu et al. | |
| 2005/0095292 A1 | 5/2005 | Benjamin et al. | |
| 2005/0100603 A1 | 5/2005 | Sako et al. | |
| 2006/0240107 A1 * | 10/2006 | Lenaerts et al. | 424/472 |

FOREIGN PATENT DOCUMENTS

| | | |
|---|---|---|
| WO | WO-2005/115387 | 12/2005 |
| WO | PCTUS2006028447 | 7/2006 |

OTHER PUBLICATIONS

Landgraft, William, et al., "Polymer Microcarrier Exhibiting Zero-Order Release", *Drug Delivery Technology*, vol. 3, No. 1, pp. 1-12, 2003.

Kollidon SR product brochure, BASF, Jun. 2008, pp. 1-12.

Examination Report for European Application No. 06800218.7 mailed Nov. 22, 2013.

Supplementary European Search Report for EP App. No. 06800218.7 mailed Mar. 29, 2012.

* cited by examiner

Formulation A

Formulation B

COATED TABLET WITH ZERO-ORDER OR NEAR ZERO-ORDER RELEASE KINETICS

RELATED APPLICATIONS

This application claims benefit of U.S. Provisional Patent Application No. 60/702,161, filed Jul. 25, 2005, the contents of which are fully incorporated herein by reference.

FIELD OF THE INVENTION

This invention relates generally to drug releasing tablets. More specifically, this invention relates to tablets for delivering water-soluble and water-insoluble drugs over a long period of time at a nearly constant rate.

BACKGROUND OF THE INVENTION

Active ingredients are commonly administered in the form of compact tablets, which release the active ingredient following oral administration. It is frequently desirable to have a steady rate of drug delivery, whether it is a zero-order release profile or a near zero-order release profile.

Numerous drug delivery devices have been prepared for obtaining steady drug delivery rates. However, many of these are incompatible with certain types of active agents, such as hydrophilic, hydrophobic or amphiphilic active agents. Further, many rely on excipients and other components, or unusual structural features, to control the release rate.

It would be advantageous to have additional drug delivery devices for providing zero-order release profiles or a near zero-order release profiles for active agents, particularly if they can be tailored for use with hydrophilic, hydrophobic and amphiphilic active agents. The present invention provides such drug delivery devices.

SUMMARY OF THE INVENTION

The present invention provides a tablet for the controlled release of an active ingredient in a zero-order or near zero-order fashion. The tablet includes a core and a coating. The core includes at least one active pharmaceutical agent and at least one hydrophilic, water-soluble, polymeric carrier. The core material is coated with a coating composition that comprises, and in some cases, consists essentially of, a cellulosic material. In some embodiments, the coating composition includes pore-forming materials, so that pores can be formed in the coating.

The active pharmaceutical agent can be hydrophilic, hydrophobic, or amphiphilic. The solubility of the active pharmaceutical agent has a bearing on the type of coating, the thickness of the coating, the loading of the agent into the hydrophilic polymer, and the like. Generally, the more water-soluble the active pharmaceutical agent is, the less water-soluble the cellulose used for the coating is, and/or the heavier the coating is. Also, the type and quantity of the hydrophilic polymer may vary depending on the water-solubility of the active pharmaceutical agent.

In one embodiment, the active pharmaceutical agent is a hydrophilic agent, and the hydrophilic polymeric carrier comprises polyethylene oxide with a number average molecular weight of between about 1,000,000 and 10,000,000, preferably between about 4,000,000 and 8,000,000. Representative polyethylene oxide polymers include polyethylene oxide N303 and polyethylene oxide N750. A mixture of polyvinylacetate and polyvinyl pyrrolidone, such as Kollidon SR, can also be used in combination with the polyethylene oxide.

When the active pharmaceutical agent is a hydrophilic agent, it is preferred that the coating comprises a relatively hydrophobic cellulose, such as ethylcellulose or propylcellulose. Surelease™ is a representative coating composition that includes ethylcellulose. However, if the tablet is uncoated, it can provide a near-zero-order release rate rather than a zero-order release rate.

The hydrophilic agents can include polysaccharides and other macromolecules such as peptides, proteins, peptidomimetics, cytokines, nucleotides, nucleosides, genetic materials, toxoids, serum vaccines or combinations thereof, and pharmaceutically acceptable salts thereof.

In another embodiment, the active pharmaceutical agent is a hydrophobic agent. In this embodiment, the hydrophilic polymeric carrier is the same as in the first embodiment, but it is preferred that the coating includes (along with or in place the alkyl cellulose) a relatively more hydrophilic cellulose, such as hydroxyethylcellulose, hydroxypropylcellulose or hydroxypropylmethyl cellulose (HPMC), or blend thereof, optionally includes other celluloses. When the active agent is hydrophobic, it may be desirable in certain embodiments to use electrolytic excipients and/or cyclodextrins.

Representative hydrophobic agents include certain anti-cancer agents, hormones, antibiotics, and benzodiazepines.

In yet another embodiment, the active pharmaceutical agent is an amphiphilic agent. In this embodiment, the hydrophilic polymeric carrier is the same as in the first embodiment, but it is preferred that the coating includes (along with or in place the alkyl cellulose) a relatively more hydrophilic cellulose, such as hydroxyethylcellulose, hydroxypropylcellulose, hydroxypropylmethyl cellulose (HPMC), or blend thereof, optionally includes other celluloses.

The core can also include non-polymeric excipients, although it can be preferred to minimize or avoid using non-polymeric excipients altogether. Viscosity-controlling agents may also be used.

In general, the release rate for the active pharmaceutical agent (whether hydrophilic, hydrophobic or amphiphilic) can be controlled by adjusting the thickness and/or composition of the coating, and, optionally, by adjusting the type and/or concentration of the polymeric and/or non-polymeric excipients.

The release rate is suppressed with the polymer in the core, because the molecular weight of the polyethylene oxide is relatively high. An additional advantage of using relatively high molecular weight polyethylene oxide is that the release is pH independent, unlike where ionic polymers such as polyacrylic acids are used. Further, active pharmaceutical agents including functional groups that might react with such polymers (i.e., that include amine and/or carboxylic acid groups) can be used without an adverse reaction between the active agent and the polymer.

While not wishing to be bound to a particular theory, it is believed that the zero-order dissolution release profile is achieved as a result of the effect of the coating layer on the core polymers, and that, in some embodiments, the effect may be more than an additive effect. While the dissolution of the water-soluble polymers begins upon contact with a liquid media the coating provides partial protection of the core polymers, thereby impeding the immediate onset of solubilization. The active pharmaceutical ingredient is also solubilized, but its release rate is thus greatly affected. It is the combination of these high molecular weight water-soluble polymers with an impeded onset of dissolution (the effect of the coating) that causes the liner/constant release rate characterized as zero-order.

As tablet size increases, so too does the thickness of the coating layer. The individual tablet surface area increases with larger tablet sizes, thus offering more exposure and opportunity for the media to begin dissolving the core tablet. By adjusting the coating thickness, and, optionally, also the types and ratios of the polymers, larger tablets can still be produced to offer a zero-order or near-zero-order dissolution rate.

The tablets can be prepared by mixing an active pharmaceutical ingredient, a polyethylene oxide with a molecular weight between about 1,000,000 and 10,000,000, and, optionally, a mixture of polyvinylacetate and polyvinyl pyrrolidone, in suitable weight ratios, to form a mixture suitable for compressing into tablet form. This mixture is then compressed and formed into tablets, and the tablets are then coated.

DETAILED DESCRIPTION OF THE INVENTION

Figure 1:
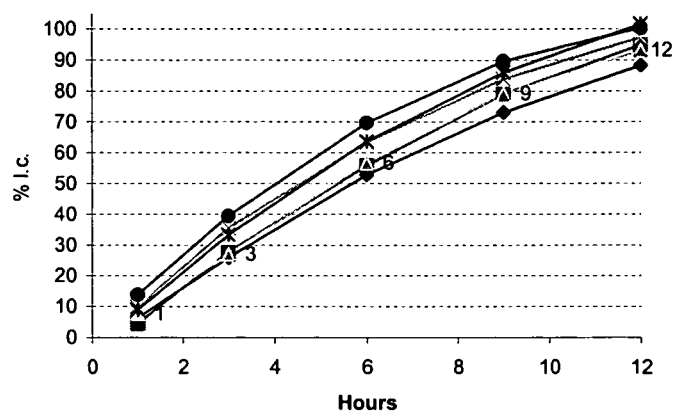
FIG. 1 is a graph of the release of a hydrophilic drug from tablets prepared according to Formulation A of Example 1. The various symbols represent the results of the dissolution of six tablets in a six-vessel dissolution bath, with one tablet in each vessel, where each shape represents the results from one vessel of the dissolution bath.

The present invention provides oral controlled drug delivery systems for highly soluble, as well as insoluble, active pharmaceutical ingredients in low or high dosage strengths that release the active ingredient in controlled zero-order/near-zero-order manner, throughout a specified timeframe. By adjusting the excipient ratios and coating level the timeframe can be varied from 3 hours to 12 hours. The drug delivery systems provide a desired release rate of the active pharmaceutical ingredient, in which the system is simple, uncomplicated and relatively easy to manufacture.

The present invention provides an oral controlled drug delivery system that is suitable for use with highly soluble actives, as well as poorly soluble actives in high or low dosage strength concentrations, and delivers a zero-order or near zero-order release rate upon dissolution. The controlled drug delivery systems comprise an active pharmaceutical ingredient in combination with water soluble (hydrophilic) polymers and other pharmaceutically acceptable excipients in a homogenous mixture which is compressed to form tablets. These tablets are coated to provide a zero-order release profile. The invention will be better understood with respect to the following detailed description.

The terms "active agent," "drug" and "pharmacologically active agent" are used interchangeably herein to refer to a chemical or biological material or compound which, when administered to an organism (human or animal, generally human), induces a desired pharmacologic effect. Combinations of these materials are also within the scope of this invention, and where the singular term is used, the plural term is also intended.

"Optional" or "optionally" means that the subsequently described circumstance may or may not occur, so that the description includes instances where the circumstance occurs and instances where it does not.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

I. Tablet Components a) Hydrophilic Polymer

The hydrophilic polymer comprises, and in some embodiments, consists essentially of, a polyethylene oxide polymer with a molecular weight in the range of between about 1,000,000 and 10,000,000, preferably between about 4,000,000 and 8,000,000.

In addition to the polyethylene oxide, a mixture of polyvinylacetate and polyvinyl pyrrolidone, such as Kollidon SR, can be used.

b) Hydrophilic Drug

Hydrophilic drugs generally have an aqueous solubility greater than about 10 g/liter. Representative drugs include polysaccharides and other macromolecular drugs such as peptides, proteins, peptidomimetics, cytokines, nucleotides, nucleosides, genetic materials, toxoids, serum vaccines, etc. Polysaccharide drugs include disaccharides, oligosaccharides, or longer chain saccharide polymers that are suitable for administration to a human being. Examples of polysaccharide drugs include, without limitation, glucosamine, glycosaminoglycans, dextran, xylan, pentasaccharide, polygalacturonic acid, polymannuronic acid, chitin, pharmaceutically acceptable salts, esters or other derivatives thereof, and combinations of any of the foregoing. That is, a single polysaccharide drug may be administered, or two or more polysaccharide drugs may be administered in combination. The polysaccharide drugs may also be fragments of naturally occurring or synthetic polysaccharides.

Preferred polysaccharide drugs are glycosaminoglycans selected from heparin, heparan, chondroitin, dermatan, hyaluronic acid and pharmaceutically acceptable salts and esters thereof. More preferred polysaccharide drugs for administration using the present dosage forms and delivery systems are heparin, low molecular weight heparin, heparan, heparin and heparan salts formed with metallic cations (e.g., sodium, calcium or magnesium, preferably sodium) or organic bases (e.g., diethylamine, triethylamine, triethanolamine, etc.), heparin and heparan esters, heparin and heparan fatty acid conjugates, heparin and heparan bile acid conjugates, heparin sulfate, and heparan sulfate. For convenience, the aforementioned more preferred polysaccharide drugs are collectively referred to herein as "heparin." The particularly preferred drug herein is low molecular weight heparin, i.e., a heparin fragment generally having a weight average molecular weight in the range of 1000 to 10,000 D. Examples of low molecular weight heparin fragments include, but are not limited to, enoxaparin, dalteparin, danaproid, gammaparin, nadroparin, ardeparin, tinzaparin, certoparin and reviparin.

Representative hydrophilic therapeutic agents include acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphiphilicin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human;

calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime; cefoxitin sodium; ceftizoxime; ceftriaxone; cefuroxime axetil; cephalexin; cephapirin sodium; cholera vaccine; chrionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; dornase alpha; doxacurium chloride; doxorubicin; editronate disodium; elanaprilat; enkephalin; enoxacin; enoxaprin sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor; granulocyte-macrophage stimulating factor; growth hormones-recombinant human; growth hormone-bovine; gentamycin; glucagon; glycopyrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; methanamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neutontin; norfloxacin; octreotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopressin derivatives; vecoronium bromide; vinblastin; vincristine; vinorelbine; vitamin B12; warfarin sodium; yellow fever vaccine; zalcitabine; zanamavir; zolandronate; and zidovudine.

c) Amphiphilic Drugs

Certain drugs are amphiphilic, rather than hydrophobic or hydrophilic. The drugs tend to include hydrophobic and/or lipophilic regions, as well as hydrophilic and/or lipophobic regions. As such, these molecules are amphiphilic in nature. Examples include polyene antibiotics such as Amphiphilicin B, analgesics such as bupivacaine, ropivacaine, prilocaine, mepivacaine, tetrocaine, etidocaine, morphine, fentanyl, alfentanil and sulfentanil.

d) Hydrophobic Drugs

Hydrophobic drugs are those with water solubility less than 10 g/liter. Examples of hydrophobic drugs include anticancer agents such as paclitaxel, camptothecin, doxorubicin, daunomycin, cisplatin, 5-fluorouracil, mitomycin, methotrexate, and etoposide; anti-inflammatory agents such as indomethacin, ibuprofen, ketoprofen, flubiprofen, diclofenac, piroxicam, tenoxicam, naproxen, aspirin, and acetaminophen; antifungal agents such as itraconazole, and ketoconazole; sex hormones such as testosterone, estrogen, progestone, progensterone, and estradiol; steroids such as hydrocortisone, dexamethasone, prednisone, prednisolone, and triamcinolone; antihypertensive agents such as captopril, ramipril, terazosin, minoxidil, and parazosin; antiemetics such as ondansetron and granisetron; antibiotics such as metronidazole, and fusidic acid; cyclosporine; and biphenyl dimethyl dicarboxylic acid. Additional examples include benzodiazepines, clofibrate, chlorpheniramine, dinitrate, digoxin, digitoxin, ergotamin tartate, fenofibrate, griseofulvin, hydrochlorothiazide, isosorbide, medrogeston, oxyphenbutazone, polythiazide, spironolactone, tolbutamide, 10,11-dihydro-5H-dibenzo[a,d]cycloheptene-5-carboxamide; 5H-dibenzo[a,d]cycloheptene-5-carboxamide, fish oil and the like.

e) Non-Polymeric Excipients

In addition to the polymers described herein, lubricants, fillers, binders and the like can be used. The concentration ranges for the filler can be up to approximately 58% by weight of the tablet. The concentration ranges for lubricants can be up to about 5% by weight, although due to the nature of the polyethylene oxide in the tablet core, in most embodiments, no lubricants need be added.

Suitable fillers include inorganic compounds such as the chloride, sulfate and phosphate salts of potassium, sodium and magnesium as well as calcium citrate, phosphate, lactate, gluconate and succinate salts.

Pharmaceutically acceptable binders suitable for use in the present formulations can be selected from those routinely used by formulation chemists and include sucrose, gelatin, acacia, tragacanth, cellulose derivatives, povidone, and other binders known to those familiar with pharmaceutical formulations.

Conventional, pharmaceutically-acceptable die wall lubricants commonly used to facilitate the ejection of tablets from the die after compression, by lubricating the tableting tool, can be used. Examples of such conventional die wall lubricants include stearate salts such as calcium, magnesium, and zinc, as well as stearic acid, mineral oil, vegetable oil derivatives, talc, and the like. In general, lubricants are present at a concentration of 0.5-5% by weight of the final tablet weight, amounts in which these ingredients function as die wall lubricants, typically 1-4 wt. %. However, as polyethylene oxide acts as a lubricant, the tablets can generally be prepared without any added lubricants.

II. Tablet Preparation

The tablets can be manufactured using means well known to those of skill in the art. There are three methods that are typically used commercially for making compressed tablets such as the drug delivery devices described herein. These include the direct compression method, the dry granulation method (also known as slugging), and the wet granulation method. Of these, slugging is preferred.

In the direct compression method, a compressible vehicle is blended with the medicinal agent, and if necessary, with a lubricant and a disintegrant, and then the blend is compressed. Substances commonly used as compressible vehicles include anhydrous lactose, dicalcium phosphate (Emcompress), granulated mannitol, microcrystalline cellulose (Avicel), compressible sugar (Di-Pac), starch (Sta-Rx 1500), hydrolyzed starch (Celutab), and blends of sugar, invert sugar, starch and magnesium stearate (Nutab).

In the dry granulation method (slugging), the ingredients in the formulation are intimately mixed and precompressed on heavy duty tablet machines. The slug which is formed is ground to a uniform size and compressed into the finished tablet.

The wet granulation method has more steps, and is more time-consuming than the other methods, and is typically not suitable for thermolabile or hydrolyzable drugs. The general steps include:

- intimately mixing the powdered ingredients by geometric dilution,
- preparing a granulating solution or binder,
- kneading the powders and the granulation solution to the desired consistency,
- forcing the wet mass through a screen or wet granulator,
- drying the resulting granules, for example, in an oven or a fluidized bed dryer,
- screening the dried granules to a suitable size for compression,
- mixing a lubricant and, optionally, a disintegrating agent, with the granulation, and
- compressing the granulation into the finished tablet.

Polymers are mixed with the active in a ratio of polymer to active of from about 0.001/1 to about 0.3/1, ideally between about 0.01/1 and about 0.1/1. The exact ratio depends on the viscosity grade of the polymer, on the tablet dimension and shape, on the desired release rate, and on the particular type of active pharmaceutical ingredient. For example, hormones and certain other drugs need only be administered in relatively low doses in order to be effective, so these can be present in ratios at the lower end of the ranges described herein.

Those of skill in the art, using the teachings herein, can readily determine suitable loadings to obtain a desired dosage and release rate.

Tablet Coating

The resulting zero-order or near-zero-order release tablets can optionally, but preferably, be coated with a solution of ethyl cellulose, or other cellulosic materials, using coating methods well known to those of skill in the art. The tablet coating processes described herein include film coating (ideally using cellulose derivatives), versus sugar coating. Tablet coating equipment may include spray guns, coating pans, polishing pans, solution tanks, blenders and mixers, homogenizers, mills, peristaltic pumps, fans, steam jackets, exhaust and heating pipes, scales and filters. One well known and particularly preferred coating method involves spray coating.

In one embodiment, a colloidal suspension or a dispersion of ethyl cellulose, optionally with additional components such as light silicic acid anhydrides, is prepared. Such light silicic acid anhydrides are described in The Pharmacopoeia of Japan XII and are commercially available under the trade name of, for example, Aerosil-200 (produced by Nippon Aerosil Co., Ltd.).

While ethyl cellulose used in the present invention is not particularly limited so long as it is capable of forming a film, an ethyl ether of cellulose having an ethoxy group content of 46 to 51% is usually employed. This type of ethyl cellulose is commercially available under the trade name, for example, of Ethocel Standard (produced by Dow Chemical Co., Ltd.) and the like.

In the present invention, the coating agent is prepared by dissolving ethyl cellulose in ethanol, or the like, usually in a total concentration of 2 to 10% by weight, preferably 4 to 7% by weight. Optionally, light silicic acid anhydride can be dispersed in the mixed solution, usually at a range of about 0.05 to 0.5 part by weight, preferably 0.1 to 0.3 part by weight. The coating agent is usually applied to the core to a coating weight of 1 to 20% by weight, preferably about 2.5 to 8% by weight, based on the weight of the core.

Tablet coating typically takes place in a controlled atmosphere inside a perforated rotating drum. Angled baffles fitted into the drum and air flow inside the drum can provide means of mixing the tablet bed. As a result, the tablets are lifted and turned from the sides into the centre of the drum, exposing each tablet surface to an even amount of deposited/sprayed coating. The liquid spray coating is then dried onto the tablets by heated air drawn through the tablet bed from an inlet fan. The air flow is typically regulated for temperature and volume to provide controlled drying and extracting rates, and at the same time, maintaining the drum pressure slightly negative relative to the room in order to provide a completely isolated process atmosphere for the operator.

Experimental procedures and the results of experiments performed according to those procedures are discussed below.

Example 1

Drug Delivery Devices Containing a Hydrophilic Drug

Figure 2:
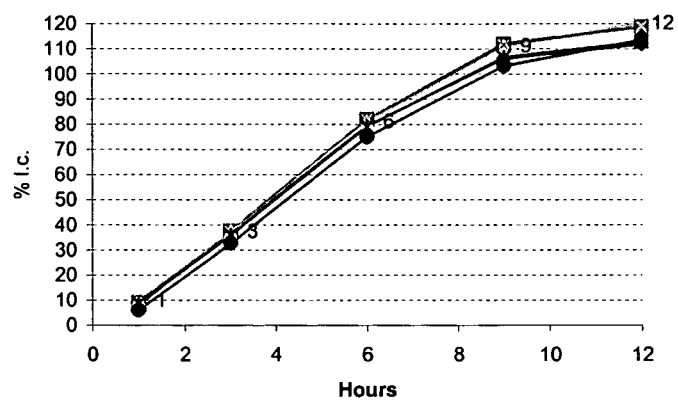
FIG. 2 is a graph of the release of a hydrophilic drug from tablets prepared according to Formulation B of Example 1. The various symbols represent the results of the dissolution of six tablets in a six-vessel dissolution bath, with one tablet in each vessel, where each shape represents the results from one vessel of the dissolution bath.

Table I shows two example formulations that were developed to obtain a zero-order/near zero-order in-vitro dissolution rate and their respective dissolution profiles (FIGS. 1 and 2). The active pharmaceutical ingredient used in each formulation was used at a low dosage strength (1 mg), and is a highly water soluble active pharmaceutical ingredient.

TABLE I

| Formulations for zero/near-zero-order release tablets | |
|---|---|
| Formulation A: | Formulation B: |
| API | API |
| Kollidon SR | Polyethylene oxide N750 |
| Polyethylene oxide N303 | Polyethylene oxide N303 |
| Emcompress | Emcompress |
| Pruv | Pruv |
| Surelease coating 3% | Surelease coating 5% |

Testing Procedure:

The release rate of the API from the tablets in Formulations A and B can be determined by dissolution. In this case, the dissolution of six tablets, one per vessel, was measured in 900 mL of dissolution media at 37° C. Samples were removed at timepoints of 1, 3, 6, 9, 12 and 24 hours. The samples were analyzed by HPLC in order to detect the concentration of the API that was released at each timepoint. The data is shown in FIGS. 1 and 2.

Although this invention has been described with reference to specific embodiments thereof, it is understood that other embodiments and variations of the invention as described and exemplified may be made by those skilled in the art without departing from the true spirit of the invention. It is intended that the appended claims be construed to include all such embodiments and variations.

The invention claimed is:

1. A zero-order or near-zero-order drug delivery device, comprising a tablet with a core formed of a mixture consisting essentially of:
   a) a hydrophilic drug;
   b) a polyethylene oxide with a molecular weight between about 1,000,000 and 10,000,000; and
   (c) a mixture consisting of 80% polyvinyl acetate, 19% polyvinyl pyrrollidone, 0.8% sodium lauryl sulfate, and about 0.2% of silica,
   wherein the core is spray coated with a pH independent ethylcellulose, and
   wherein the device erodes at a zero-order or near zero-order release rate upon ingestion, thereby releasing the hydrophilic drug at a zero-order or near zero-order delivery rate.

2. The device of claim 1, wherein the polyethylene oxide has a molecular weight between about 4,000,000 and 8,000,000.

3. The device of claim 1, wherein the polyethylene oxide has a molecular weight of 7,000,000.

4. The device of claim 1, wherein the tablet coating comprises an aqueous ethylcellulose dispersion.

5. The device of claim 1, wherein the hydrophilic drug is present in a range of between about 1 and 10 percent by weight of the tablet.

6. The device of claim 1, wherein the release is zero-order.

7. The device of claim 1, wherein the hydrophilic drug is selected from the group consisting of polysaccharides, peptides, proteins, peptidomimetics, cytokines, nucleotides, nucleosides, genetic materials, toxoids, serum vaccines, combinations thereof, and pharmaceutically acceptable salts thereof.

8. The device of claim 1, wherein the core controls the hydrophilic drug rate of release.

9. The device of claim 1, wherein the ethylcellulose is present in a range of between about 1 and 20 percent by weight of the core.

\* \* \* \* \*